United States Patent [19]
Scatizzi et al.

[11] Patent Number: 6,105,636
[45] Date of Patent: Aug. 22, 2000

[54] APPARATUS FOR THE CONTROLLED WITHDRAWAL AND DELIVERY OF VOLUMETRICALLY METERED LIQUIDS

[75] Inventors: Mario Scatizzi, Pistoia; Mauro Anguillesi, Prato; Moreno Bartalucci, Florence, all of Italy

[73] Assignee: Technorama S.R.L., Prato, Italy

[21] Appl. No.: 09/266,522

[22] Filed: Mar. 11, 1999

[30] Foreign Application Priority Data

Mar. 26, 1998 [IT] Italy .................................. FI98A0070

[51] Int. Cl.[7] ....................................... B65B 1/04
[52] U.S. Cl. .............................. 141/130; 141/27; 422/99; 422/100
[58] Field of Search .................... 141/21, 25, 27, 141/98, 130, 104; 422/99, 100, 102, 64

[56] References Cited

U.S. PATENT DOCUMENTS

| | | | |
|---|---|---|---|
| 4,456,037 | 6/1984 | Gocho | 141/1 |
| 5,479,969 | 1/1996 | Hardie et al. | 141/130 |
| 5,555,920 | 9/1996 | Godolphin et al. | 141/130 |
| 5,645,114 | 7/1997 | Bogen et al. | 141/145 |

*Primary Examiner*—Steven O. Douglas
*Attorney, Agent, or Firm*—McGlew and Tuttle, P.C.

[57] ABSTRACT

Apparatus for the controlled withdrawal and delivery of volumetrically metered liquids of a type comprising a support structure able to receive a first series of vessels or bottles which contain substances in a liquid phase, and a second series of vessels or glasses able to receive one or more said substances in preset doses, means being provided for withdrawing and feeding said substances in preset doses and able to withdraw said substances individually from said bottles and discharge them into said glasses, apparatus characterized in that said withdrawal and delivery means comprise a series of single withdrawal and delivery members (7) able to be positioned in correspondence of each of said bottles and resolvably matchable with an actuation and driving head (6).

20 Claims, 3 Drawing Sheets

APPARATUS FOR THE CONTROLLED WITHDRAWAL AND DELIVERY OF VOLUMETRICALLY METERED LIQUIDS

FIELD OF THE INVENTION

The present invention refers to an apparatus for the controlled withdrawal and delivery of volumetrically metered liquids.

BACKGROUND OF THE INVENTION

Existing apparatus for volumetric metering, especially of the type used in the preparation of dye solutions for dyeing textile materials, comprise essentially a structure with a platform having vessels or "bottles" disposed thereon which contain the solutions. Each vessel contains one solution corresponding to a predetermined colour and being located in a fixed and preset position of the platform. Provided in a separate station of the same platform, in correspondence of fixed and preset positions, are vessels or "glasses" intended to receive the solutions drawn from the bottles in preset doses. The withdrawal and metering of the solutions are operated by means of a syringe or "pipette" movable on the platform between the bottles containing the solutions to be drawn therefrom and the glasses which receive them in preset doses. An electronic processor or computer controls the movements of the pipette between the various sites on the platform.

In order to use the same syringe upon the removal and metering of different solutions, a washing is to be carried out each time by means of a suitable solvent to avoid detrimental solutions contaminations. Such an apparatus is disclosed in the document EP-A-0,602,737.

A drawback stemming from the use of an apparatus of the type above described is the fact that whenever the syringe is washed, there is a loss of residual liquid, that is, the liquid exceeding the dose to be taken into the glasses, which residue is ejected together with the solvent and collected in a drain duct for subsequent disposal thereof along with other elements.

A further drawback lies in the general slowing down of the operations due to the time and care required to carry out a proper washing of the syringe. Besides, it is not to be fully excluded the possibility that the solutions will be contaminated all the same, since, subsequently to the washing, the syringe chamber may still exhibit some amounts of residual solvent.

It should also be noted that by using this type of apparatus for the volumetric metering of liquids such as essence and perfume solutions, each washing requires a huge quantity of solvent, or alcoholic products, which are more expensive than water. In this industrial sector, the problem of possible contamination of different solutions to be treated is in fact particularly felt, and such contaminations may bring about damages which are more serious than in the case of preparing dye solutions for dyeing textile materials.

SUMMARY AND OBJECTS OF THE INVENTION

The object of the present invention is to overcome the drawbacks.

This result has been achieved, according to the invention, by adopting the idea of making an apparatus having a support structure with a first and second plurality of vessels. Each of the first plurality of vessels includes a withdrawal and delivery member. A transporter on the support structure selectively connects to each of the withdrawal and delivery members, and selectively transfers substances from one of the first plurality of vessels into one of the second plurality of vessels using a respective withdrawal and delivery member of the one of the first plurality of vessels. Further characteristics being set forth in the depending claims.

The advantages deriving from the present invention lie essentially in the fact that it is possible to completely eliminate the need of carrying out the washing of the syringes, which implies a significant reduction in the operational times and, thereby, a corresponding increase of the production capacity of the apparatus and the total elimination of the risk of solutions contamination; that an apparatus according to the invention is easy to make, cost-effective and reliable even after a prolonged service life; that it is possible to treat, that is, withdraw and meter, with maximum accuracy and without any possibility of contamination, liquids of any type, such as dyeing solutions for dyeing operation and solutions for the perfume or pharmaceutical industry.

These and other advantages and characteristics of the invention will be best understood by anyone skilled in the art from a reading of the following description in conjunction with the attached drawings given as a practical exemplification of the invention, but not to be considered in a limitative sense.

DESCRIPTION OF THE PREFERRED EMBODIMENT

Figure 1:
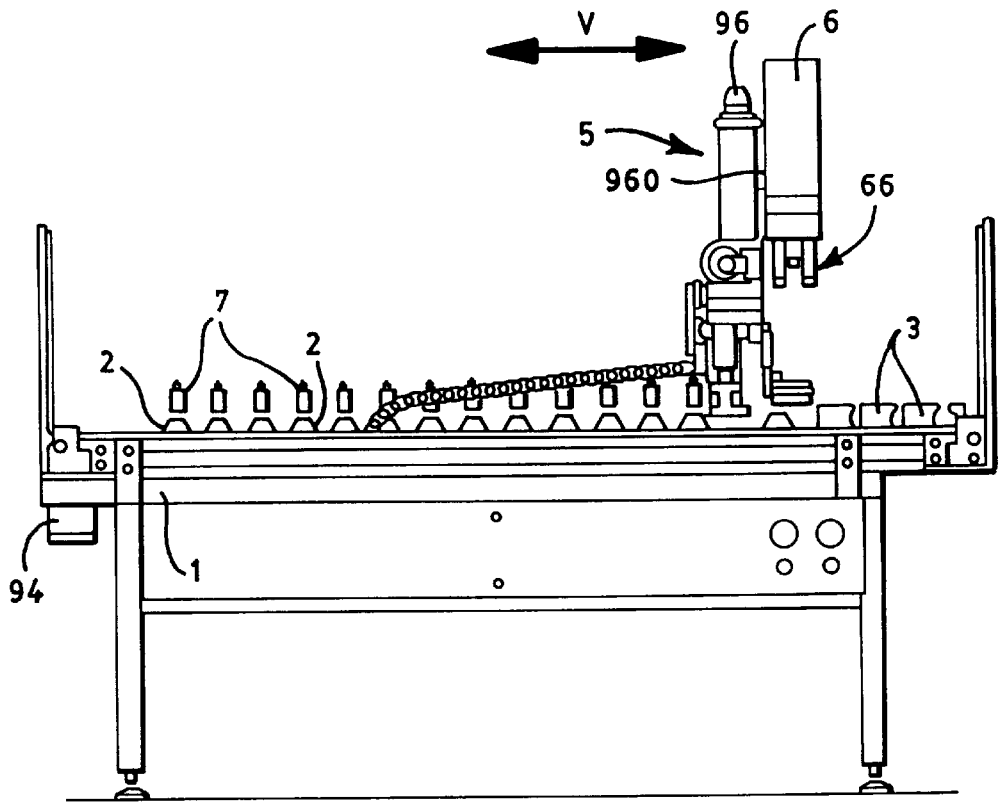
FIGS. 1, 2 are respectively, a side view and a top view of a feasible embodiment of an apparatus according to the invention.
Figure 2:
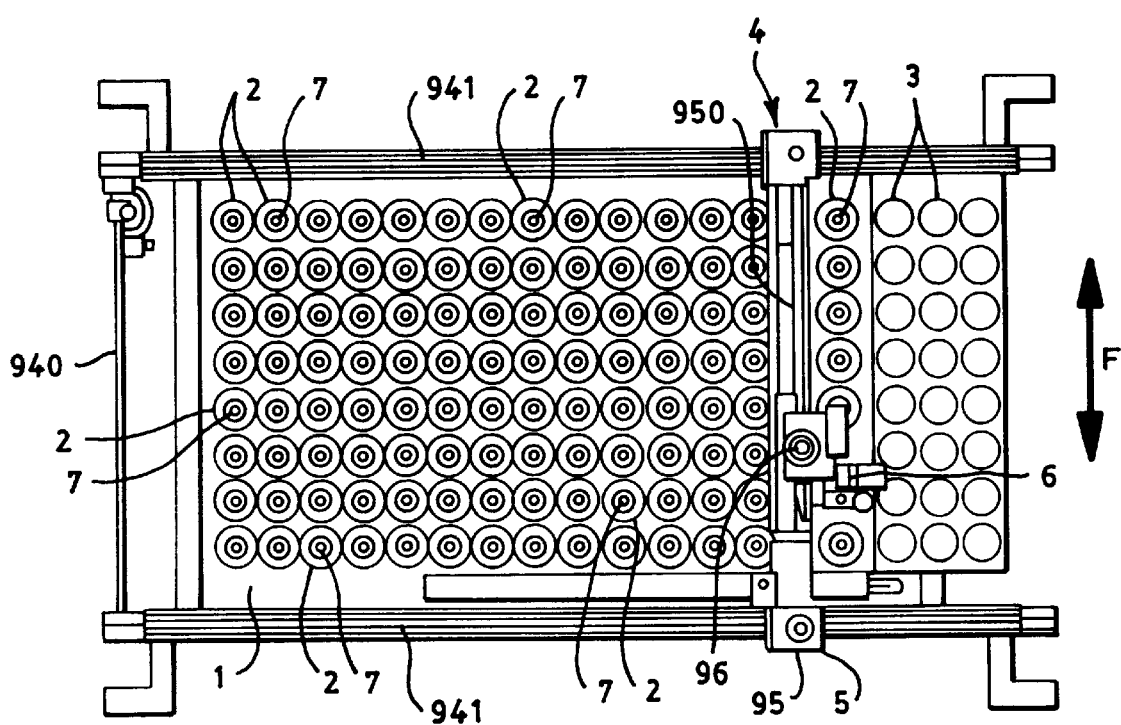

With reference to the accompanying drawings which, as set forth above, refer to one of possible embodiments, the present invention concerns an apparatus for the controlled withdrawal and delivery of volumetrically metered liquids. The apparatus comprises a support structure (1) defining a plane on which a series of first vessels (2) and a series of second vessels (3) may be disposed. The first vessels, also referred to as bottles (2) in this description, contain substances in liquid phase to be suitably combined by introducing them into the second vessels (3) (indicated as glasses hereinafter). In order to transfer the substances held in the bottles (2) into the glasses (3), withdrawal means, or transporter, are provided comprising at least a bridge (4) movable in two directions on the structure (1), according to the longitudinal development of the same structure, under control of relevant motive members (94) for example of electrical type, with a rod (940) and transmission belts (941) for movement in direction V. The bridge element (4) supports a movable equipment (5) able to move along the bridge element (4) along a direction (F) transverse to the longitudinal development of the structure (1) and, therefore, orthogonally to the above direction (V), under control of a motive member (95) of electrical type, for example, with relevant transmission annular belt (950). In practice, the movable equipment is made to move on the plane of the structure (1) along the two dimensions thereof. Moreover, in correspondence of the movable equipment (5) there is provided a clamping head (6), also referred to as moving and operating head (6), associated to relevant motive members (96), of electrical type for example. The head is vertically movable (in a direction indicated by z in FIGS. 3b and 3d) onto a corresponding straight guide (960), close to and away from the plane of the structure (1) on which the vessels (2, 3) are disposed. The clamping head (6) has two arms (66) able to be moved under control close to and away form each other, for example in the direction indicated by (P) in FIG. 3a, so as to define a clamping member for a series of individual withdrawal and delivery members consisting, for example, of syringes (7) provided in correspondence of each bottle (2). The individual withdrawal and delivery members may also consist of pipettes or similar elements.

Under a rest condition, each syringe (7) is inserted into the access aperture (8) of the relevant bottle (2), and the relevant needle (77) is dipped into the substance held in the same bottle. The syringe (7) has a peripheral portion or collar of larger cross-section (78) and of such dimensions as to completely occlude the opening of the bottle (2). This feature allows the bottle (2) to be tight-sealed thereby preventing any possible leak due to evaporation of the substances held therein.

Figure 3A:
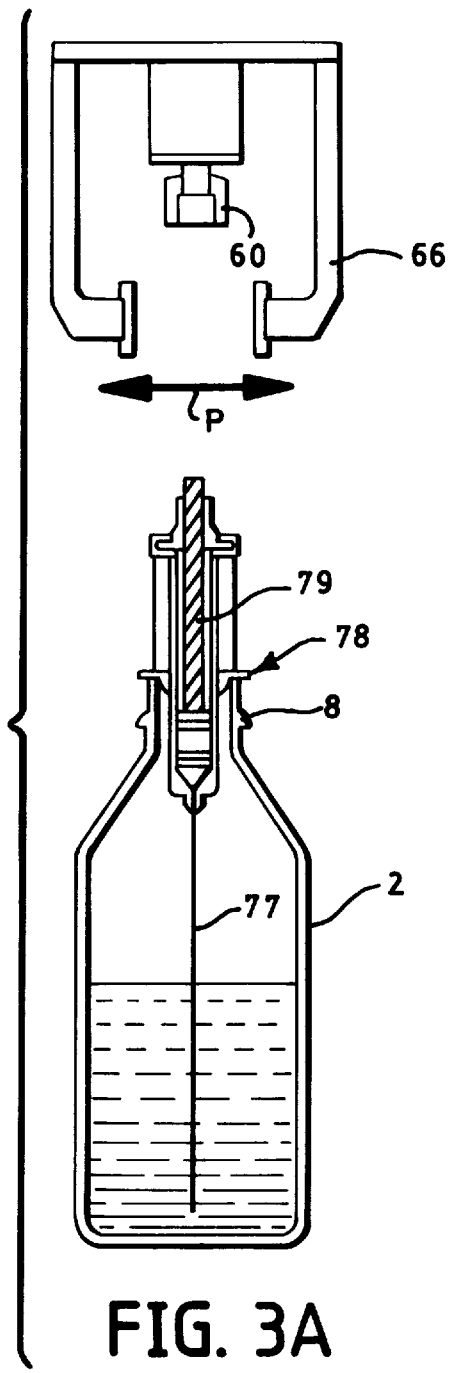
FIGS. 3a, 3b, 3c and 3d show in schematic side view sequential stages for the withdrawal of a liquid from a storage vessel or bottle.
Figure 3B:
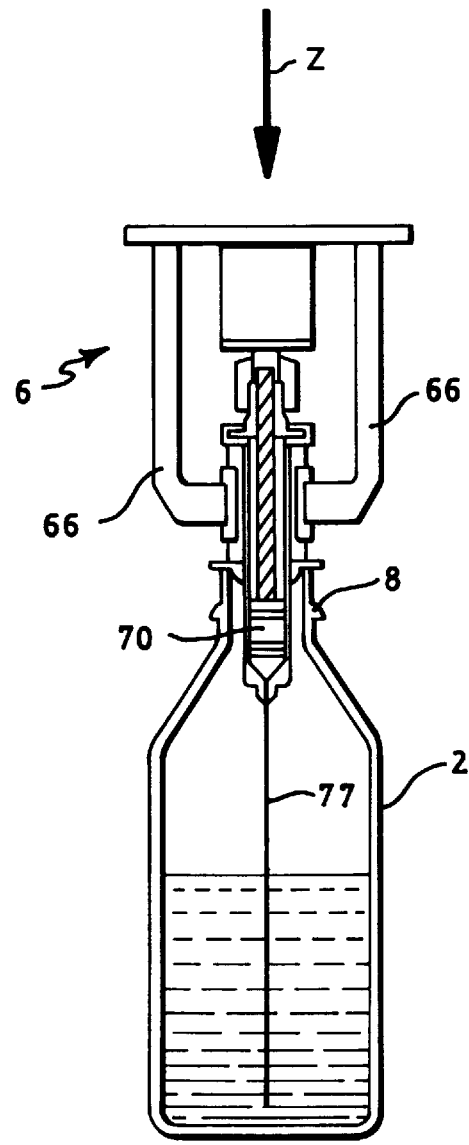
Figure 3C:
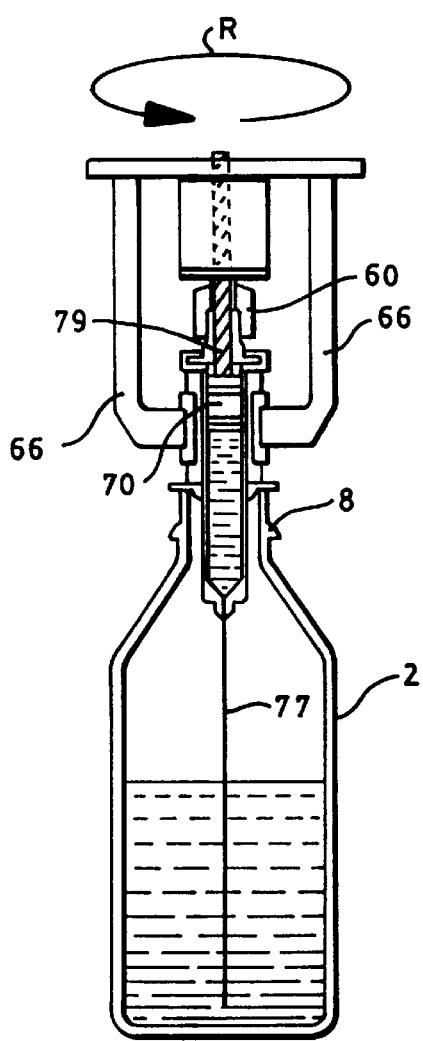
Figure 3D:
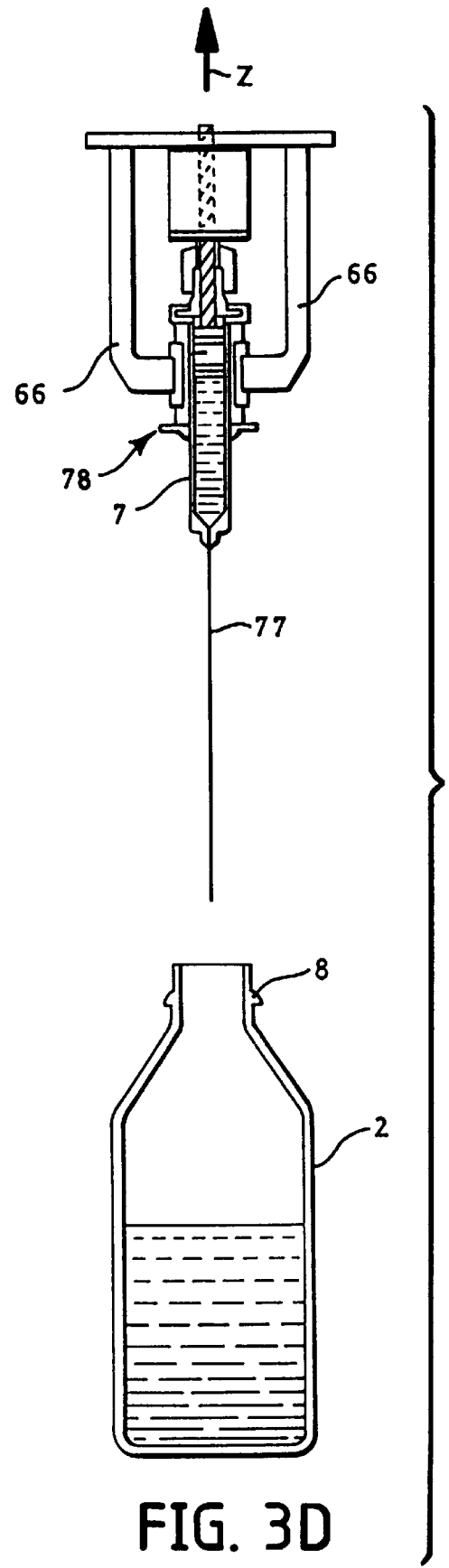

Upon the withdrawal of the substance contained in a given bottle, the movable equipment (5) is brought in correspondence of the selected bottle (2) and the clamping head (6) is moved downwards as illustrated in FIGS. 3a and 3b. Above its own plunger (70), the syringe (7) has a moving portion (79) provided with a thread that defines a screw nut on which suitable screw means (60) are made to act via a corresponding stepping motor (9). The action of the screw means (60) drives the moving portion (79) and the plunger (70) solid thereto into a vertical displacement; in this way, it is possible either to fill in or empty out the syringe (7) in correspondence of an upwards or downwards movement, as well as to withdraw or feed a predetermined dose. As the withdrawal operations go on, according to what is illustrated in FIGS. 3c and 3d, the screw means (60) are operated to fill the syringe (7) with the preset dose of liquid contained in the selected bottle. Finally, the clamping head is lifted up in the direction (2) shown by the arrow, and the movable equipment (5) is moved along with the syringe (7) toward the glass (3) which is to receive the removed substance. Once the syringe (7) has been emptied out of its content (that is, after feeding the preset dose), it is brought back to its rest position.

To operate the means which drive the movable equipment (5) and the clamping head (6), use can be made of a programmable electronic unit (not represented in the figures of the attached drawings) having a memory for storing data relevant to the positions of the bottles (2) and glasses (3) and the values relevant to the preset doses, that is, to the extent of the stroke of plunger (70) of each syringe (7). All the above mentioned motive members are associated to the programmable unit. The latter, being known per se to those skilled in the art, is not described in greater detail.

Practically, all the construction details may vary in any equivalent way as far as the shape, dimensions, elements disposition, nature of the used materials are concerned, without nevertheless departing from the scope of the adopted solution idea and, thereby, remaining within the limits of the protection granted to the present patent for industrial invention.

What is claimed is:

1. Apparatus for the controlled withdrawal and delivery of volumetrically metered liquids of a type comprising a support structure able to receive a first series of vessels or bottles which contain substances in a liquid phase, and a second series of vessels or glasses able to receive one or more said substances in preset doses, means being provided for withdrawing and feeding said substances in preset doses and able to withdraw said substances individually from said bottles and discharge them into said glasses, apparatus characterized in that said withdrawal and delivery means comprise a series of single withdrawal and delivery members able to be positioned in correspondence of each of said bottles, each of said single withdrawal and delivery members being resolvably matchable with an actuation and driving head, under a rest condition each of said single withdrawal and delivery members being inserted through an access aperture of a relevant bottle and a relevant needle being dipped into a substance held in the relevant bottle.

2. Apparatus according to claim 1, characterized in that said individual withdrawal and delivery members are shaped substantially as a syringe.

3. Apparatus according to claim 2, characterized in that said individual withdrawal and delivery members have a plunger solid to a threaded portion defining a screw nut, said head being provided with screw means complementary to said screw nut and able to move said plunger in two directions during the withdrawal and delivery operations.

4. Apparatus according to claim 2, wherein said individual withdrawal and delivery members are provided with means for closing said bottles.

5. Apparatus according to claim 1, wherein said individual withdrawal and delivery members are provided with means for closing said bottles.

6. Apparatus according to claim 5, wherein said bottles have each an access aperture, characterized in that said closing means consist of a portion or collar of larger cross-section exhibited by said individual withdrawal and delivery members which is able to define a plug for said aperture of the bottles.

7. Apparatus according to claim 1, characterized in that said head is provided with two arms able to individually clamp said withdrawal and delivery members.

8. A dosing apparatus comprising:
   a support structure;
   a first plurality of vessels positionable on said support structure, each of said first plurality of vessels including a withdrawal and delivery member;
   a second plurality of vessels positionable on said support structure, each of said second plurality of vessels being receivable of each of said withdrawal and delivery members;
   a transporter on said support structure selectively connectable to each of said withdrawal and delivery members and selectively transfers substances from one of said first plurality of vessels into one of said second plurality of vessels using a respective said withdrawal and delivery member of said one of said first plurality of vessels.

9. The dosing apparatus in accordance with claim 8, wherein:
   said transporter transfers a substance from said one of said first plurality of vessels into a respective said withdrawal and delivery member, selectively transports said respective withdrawal and delivery member with the substance from said one of said first plurality of vessels to said one of said second plurality of vessels, and transfers the substance from said respective withdrawal and delivery means to said one of said second plurality of vessels.

10. The dosing apparatus in accordance with claim 9, wherein:
   said transporter returns said respective withdrawal and delivery means to said respective first vessel for reuse.

11. The dosing apparatus in accordance with claim 8, wherein:

each of said first plurality of vessels holds a respective said withdrawal and delivery means.

12. The dosing apparatus in accordance with claim 8, wherein:

each of said withdrawal and delivery means include a closure member for closing a respective said one of said first plurality of vessels.

13. The dosing apparatus in accordance with claim 8, wherein:

each of said withdrawal and delivery means include a syringe with a plunger solid to a threaded portion defining a screw nut;

said transporter includes a head with screw means complementary to said screw nut and able to move said plunger in two directions during transfer operations of the substances.

14. The dosing apparatus in accordance with claim 8, wherein:

said transporter transfers volumetrically metered liquids as the substances in said first plurality of vessels.

15. A process for dosing substances, the process comprising the steps of:

providing a first plurality of vessels;

providing each of said first plurality of vessels with a separate withdrawal and delivery member;

providing a second plurality of vessels receivable of each of said withdrawal and delivery members;

selectively transferring a substance from one of said first plurality of vessels to one of said second plurality of vessels using a respective said withdrawal and delivery member of said one of said first plurality of vessels.

16. The process in accordance with claim 15, further comprising;

returning said respective withdrawal and delivery means to said respective first vessel;

selectively transferring another substance from another one of said first plurality of vessels;

reusing said respective withdrawal and delivery means for transferring a substance from said one vessel to another one of second vessel.

17. The process in accordance with claim 15, wherein:

said transferring includes transferring a substance from said one of said first plurality of vessels into a respective said withdrawal and delivery member, selectively transporting said respective withdrawal and delivery member with the substance from said one first vessel to said one of said second plurality of vessels, and transferring the substance from said respective withdrawal and delivery means to said one of said second plurality of vessels.

18. The process in accordance with claim 17, wherein:

said transferring includes volumetrically metering liquids as the substances from said one of said first vessels into said respective withdrawal and delivery means.

19. The process in accordance with claim 17, wherein:

said transferring includes volumetrically metering liquids as the substances from said withdrawal and delivery means into said one of said second vessels.

20. The process in accordance with claim 15, wherein:

said transferring includes volumetrically metering liquids as the substances in said first plurality of vessels.

* * * * *

UNITED STATES PATENT AND TRADEMARK OFFICE
CERTIFICATE OF CORRECTION

PATENT NO. : 6,105,636
DATED : August 22, 2000
INVENTOR(S) : SCATIZZI et al.

It is certified that error appears in the above-indentified patent and that said Letters Patent is hereby corrected as shown below:

On the title page:
[73] Assignee: Tecnorama S.R.L., Prato, Italy

Signed and Sealed this

First Day of May, 2001

Attest:

NICHOLAS P. GODICI

*Attesting Officer*   *Acting Director of the United States Patent and Trademark Office*